US006979310B2

(12) United States Patent  
Navelier et al.

(10) Patent No.: US 6,979,310 B2  
(45) Date of Patent: Dec. 27, 2005

(54) NEEDLELESS SYRINGE WITH MEMBRANE ISOLATING A MULTIPLE DUCT INJECTOR

(75) Inventors: Alain Navelier, Pierrefeu du Var (FR); Patrick Alexandre, Gray (FR); Bernard Brouquieres, Toulon (FR); Philippe Gautier, Le Plessis Pate (FR)

(73) Assignee: CROSSJECT, Paris (FR)

( * ) Notice: Subject to any disclaimer, the term of this patent is extended or adjusted under 35 U.S.C. 154(b) by 0 days.

(21) Appl. No.: 10/258,884

(22) PCT Filed: May 29, 2001

(86) PCT No.: PCT/FR01/01645

§ 371 (c)(1), (2), (4) Date: Oct. 30, 2002

(87) PCT Pub. No.: WO01/91835

PCT Pub. Date: Dec. 6, 2001

(65) Prior Publication Data

US 2003/0097093 A1  May 22, 2003

(30) Foreign Application Priority Data

May 30, 2000  (FR) .................................. 00 06925

(51) Int. Cl.[7] ............................................. A61M 5/30
(52) U.S. Cl. ............................. 604/70; 604/68; 604/69
(58) Field of Search ........................... 604/60–72, 318, 604/135, 141–140

(56) References Cited

U.S. PATENT DOCUMENTS

| 2,605,763 | A | * | 8/1952 | Smoot | ........................ 604/70 |
| 2,764,977 | A | | 10/1956 | Ferguson | |
| 2,800,903 | A | * | 7/1957 | Smoot | ........................ 604/68 |
| 4,124,024 | A | | 11/1978 | Schwebel et al. | |
| 4,966,581 | A | | 10/1990 | Landau | |
| 5,074,843 | A | * | 12/1991 | Dalto et al. | ................... 604/68 |
| 5,769,138 | A | | 6/1998 | Sadowski et al. | |
| 6,620,135 | B1 | * | 9/2003 | Weston et al. | .............. 604/140 |

FOREIGN PATENT DOCUMENTS

| FR | 2 629 348 A2 | 10/1988 |
| FR | 2 641 190 A1 | 7/1990 |
| GB | 971162 | 9/1964 |
| WO | WO 96/15821 | 5/1996 |
| WO | WO 00/33899 | 6/2000 |

* cited by examiner

*Primary Examiner*—Nicholas D. Lucchesi  
*Assistant Examiner*—Roz Maiorino  
(74) *Attorney, Agent, or Firm*—Oliff & Berridge, PLC

(57) ABSTRACT

The invention concerns the field of needleless syringe having an injector with several ducts. The problem that needs to be solved is the long term compatibility of the injector with the liquid active principle. For that purpose the syringe (1) comprises a cylindrical reservoir (2), closed at its upstream part by a closure element (3) capable of being moved by driving means (70), and closed at its downstream part by an injector (4) comprising at least an injection duct and said reservoir being secured to the body (8) of the syringe, said syringe is such that the diaphragm (5), compatible with the active principle, isolates the latter from the injector (4) and said diaphragm can be passed through by the liquid (6) when pressurized for injection.

13 Claims, 1 Drawing Sheet

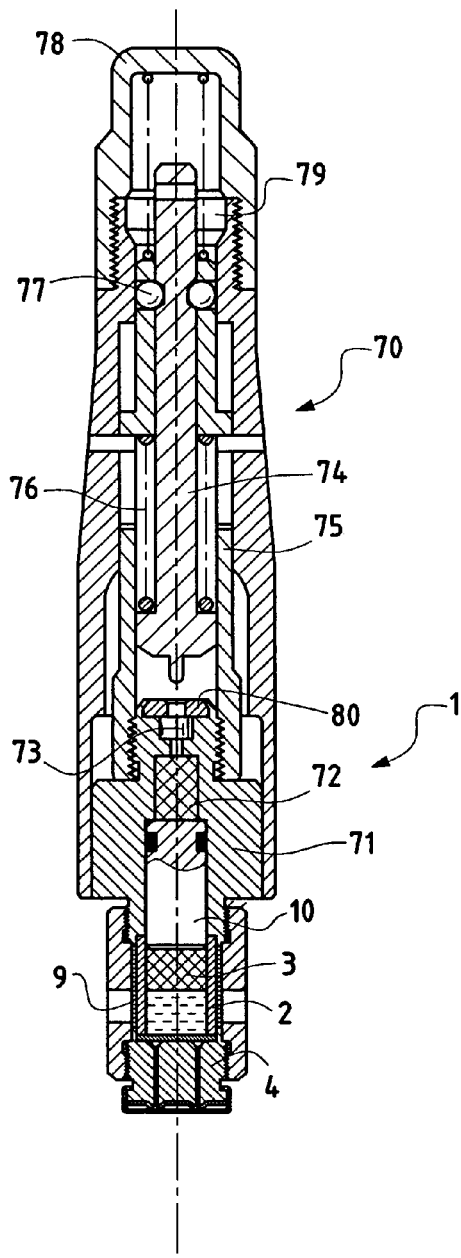

NEEDLELESS SYRINGE WITH MEMBRANE ISOLATING A MULTIPLE DUCT INJECTOR

The present invention concerns the field of prefilled and disposable needleless syringes; such syringes are used for intradermal, subcutaneous and intramuscular injections of liquid active principle intended for therapeutic use in human or veterinary medicine.

A first imperative for prefilled syringes is that of the compatibility in the long term, generally three years, between the liquid active principle and the reservoir which contains it. Another imperative, associated with the prefilling method, is that of having a transparent reservoir in order to be able to carry out the regulatory checks of correct filling of the reservoir before it is fitted in the syringe. These imperatives result in the production of a reservoir which is substantially transparent and made of a material which is compatible with the active principle for the desired length of time; this material is generally glass for pharmaceutical use: glass of type I or II. However, this poses the problem of the mechanical resistance of this reservoir to the high operating pressure required for needleless injection.

The patent EP 792 174 describes a needleless syringe in which the ampule containing the active principle is made of glass, this ampule being partially cylindrical, and its downstream part being of conical shape with, at its end, a single, very short injection duct: namely an injection orifice. This ampule is fritted, on its cylindrical part, into a compression piece. This device solves, on the one hand, the problems of long-term compatibility between the active principle and the reservoir and, on the other hand, the problems of the resistance of the reservoir to the operating pressure. However, this arrangement cannot be transposed to a syringe having several injection ducts and, more particularly, ducts which are long in relation to their diameter in order to control the distance of coherence of the jets and the depth of penetration of the jets into the skin of the subject who is being treated. To form several long ducts in a reservoir which is resistant to the high operating pressures of needleless syringes, one is forced to modify the organization of the reservoir with an essentially tubular and, if appropriate, transparent part and an injector resistant to the pressure, but not necessarily made of a material compatible in the long-term with the active principle, and thus with an additional means for re-establishing this compatibility.

The present invention concerns a needleless syringe for injection of a liquid active principle contained in a cylindrical reservoir closed at its upstream part by a closure element which can be displaced by a driving means, and closed at its downstream part by an injector which comprises at least one injection duct, and this reservoir being made integral with the body of the syringe, said syringe being characterized in that a membrane, compatible with the liquid active principle, isolates the latter from the injector, and in that said membrane can be passed through by the liquid when pressurized for injection.

In this invention, liquid active principle will be understood to mean a more or less viscous liquid, or a mixture of liquids, or a gel. It will be possible for the active principle to be a solid dissolved in a solvent suitable for injection. It will be possible for the active principle to be a powdered solid in more or less concentrated suspension in a suitable liquid. The particle size of the solid active principle and the shape of the duct must be adapted to avoid blockages.

The means which will act on the displaceable closure element can be of the mechanical type: release of a compressed spring, or of the pneumatic type: release of compressed gas, or of the pyrotechnic type: release of combustion gas.

The injector must comprise several injection ducts whose length and shape make it possible to control the distance of coherence of the jet. The injector must resist the operating pressure. The material chosen for making it must satisfy these two requirements. By contrast, it is not necessary for this material to be compatible with the active principle over a long period of time: the traversable membrane which isolates the injector from the active principle will permit this compatibility over a long period of time. The material of the membrane will be chosen from among the materials in the pharmacopeia which are known to be compatible with the active principle, for example elastomers of the type used to make the plunger stoppers in prefilled syringes, or silicones, or polytetrafluoroethylenes (PTFE). The cylindrical reservoir which will contain the active principle can be made of glass or of any other transparent material compatible with the active principle. The reservoir will itself be able to resist the operating pressure or will be arranged, in a suitable manner, in another element of the syringe allowing it to resist the operating pressure.

Advantageously, in this syringe, the traversable membrane ensures the leaktightness between the reservoir and the injector. The leaktightness is ensured either by the membrane being pinched between the reservoir and the injector, in which case the membrane then acts as a leaktight seal, or by the membrane being engaged in the reservoir, in which case it acts as a stopper.

In a first embodiment, the membrane is quite thin so that it pierces, opposite the injection ducts, when the liquid is brought under high pressure for the purpose of carrying out the injection.

In a second embodiment, the membrane comprises a zone of lesser thickness opposite each injection duct; each of these zones pierces, as before, at the moment of pressurization. For the correct functioning of this embodiment, the membrane must be well positioned, by appropriate devices, such that each zone of lesser thickness lies opposite an injection duct. A zone of lesser thickness is a blind cavity formed in the membrane, where the base of this cavity can be directed either toward the liquid or toward the upstream face of the injector and more precisely an injection duct. One of the simplest configurations is that of a cone or a truncated cone.

In a third embodiment, the membrane comprises pre-pierced areas opposite each injection duct. The elasticity of the elastomer of the membrane keeps each of the pre-pierced areas closed and, if appropriate, this closure is leaktight. When the liquid is pressurized upon triggering of the driving means, each pre-pierced area opens.

The membrane covers at least two injection ducts, the upstream ends of which are situated on the same circle centered on the axis of the cylindrical reservoir.

The zones of lesser thickness of the membrane advantageously join and form a circular groove centered on the axis of the reservoir. This circular zone is opposite the upstream ends of the injection ducts, these ends themselves being distributed on the same circle. As before, for a zone of lesser thickness the opening of the circular groove of the membrane is directed either toward the liquid or toward the upstream face of the injector.

The membrane also advantageously comprises a circular slit centered on the axis of the reservoir, this slit being opposite the upstream ends of the injection ducts, these ends themselves being distributed on the same circle. Here once again, the elasticity of the material of the membrane keeps the slit closed and, if appropriate, in a leaktight manner. When the liquid is pressurized upon triggering of the driving means, the liquid will spread the edges of the slit apart and will pass into the injection ducts.

Advantageously, the membrane which isolates the injection from the active principle bears at least partially on the upstream face (or inner face) of said injector.

Each injection duct preferably comprises, at its upstream end, an inlet cavity which will facilitate the piercing of the membrane or the opening of the pre-pierced area of the membrane at the moment of pressurization of the liquid for injection. This inlet cavity can also be common to several ducts, for example an annular groove supplying several ducts, or even all of them. This arrangement solves the problem of the positioning of the membrane relative to the injection. The shape of this cavity or of this groove is optimized to permit effective opening of the membrane and also to form a cavity at the head of the duct which makes it possible to control the distance of cohesion of the jet of liquid emerging at the other end of the duct.

For example, the inlet cavity, at the upstream end of the injection duct, is delimited by a surface of revolution whose height and diameter at the level of the upstream face of the injector are greater than the thickness of the traversable membrane but remain less than 2 or 3 times this thickness.

In the case of a circular groove for supplying the injection ducts, the optimized profile of the groove is a profile whose height and width, measured along a radius of the injector, are greater than the thickness of the membrane and remain less than 2 or 3 times this thickness.

In a different embodiment of the invention, the upstream face of the injector or inner end of the injector comprises protuberances directed toward the inside of the reservoir. The injection ducts open into the reservoir through these protuberances. These protuberances can be individual, that is to say one protuberance for each duct, or can be common to several or all of the ducts, for example in the form of an annular protuberance common to all the ducts arranged on a circumference centered on the axis of the reservoir. The traversable membrane which isolates the liquid active principle from the injector initially bears on the protuberances.

When the liquid is pressurized to carry out the injection, the membrane displaces and crushes against the protuberances, which pierce it or open the pre-pierced areas of said membrane.

As before, the membrane can comprise zones of lesser thickness arranged opposite each protuberance, in which case it is necessary to have relatively precise indexing of the zones of lesser thickness and of the protuberances: each of these zones will be pierced or torn by the corresponding protuberance. The membrane can also comprise a single zone of lesser thickness in the form of a groove: this zone will be pierced or torn by the protuberances when the liquid is pressurized.

The traversable membrane can comprise pre-pierced areas which remain closed until the liquid is pressurized. These pre-pierced areas can be individual in the sense that each pre-pierced area lies opposite one protuberance; it is then necessary to have relatively precise indexing of the membrane in relation to the protuberances. These pre-pierced areas can be common to all the protuberances, for example in the form of an annular slit opposite all the protuberances or even one annular protuberance.

According to a first variant, the driving means acts directly on the upstream closure element in order to carry out the injection.

According to a second variant, the driving means acts on the upstream closure element by way of a plunger.

The driving means is preferably a pyrotechnic gas generator. Such a device is quite compact, powerful and in particular very reliable.

The reservoir and the body of the syringe advantageously form a single unit.

The reservoir is fritted in the body via an intermediate material when the syringe, with the reservoir, is mounted on the driving means.

The body of the syringe is transparent, making it possible to view the reservoir of active principle until injection. The body comprises at least one window for viewing the contents of the reservoir when the material of the body of the syringe is not transparent.

The plunger acting on the upstream closure element advantageously serves as an indicator of the functioning of the syringe, by appearing in the transparent part or in the window of the body of the syringe.

The present invention solves the problems posed. It proposes a prefilled syringe whose reservoir is made of a material compatible with the active principle and whose injector, comprising several injection ducts, resists the high operating pressure, the problem of the compatibility of this element being solved by the interposition of a traversable membrane which is compatible with said active principle.

The present invention also has the advantage of making it possible to separate two parts in the device. One part, which will be called the pharmaceutical part, comprising the body, the injector, its membrane and the reservoir with the displaceable closure element upstream: this subunit will be able to be treated under pharmaceutical industry conditions, in particular as regards sterilization and asepsis. This subunit will be made integral with the rest of the syringe, the elements of which have been assembled elsewhere, this assembling being done under conditions which are less stringent than those associated with the pharmaceutical industry.

Finally, this configuration has the advantage of preventing any loss of liquid through the injection ducts before the injection is carried out. The device is in fact often shaken (this is even recommended) in order to examine the turbidity of the liquid or to homogenize the mixture when the liquid comprises particles in suspension. The fact that the active principle, before injection, is isolated from the ducts affords the ultimate protection against this risk of loss during the manipulations which precede application of the device to the skin of the subject who is to be treated.

The invention is explained in detail below with the aid of figures showing different particular embodiments of the invention.

FIG. 1 shows diagrammatically, and in partial cross section, a particular embodiment of a needleless syringe according to the invention.

FIG. 2 shows in detail that part of the syringe comprising the reservoir of active principle, the membrane and the injector.

FIG. 3 illustrates the deformation of the membrane opposite the upstream cavity of an injection duct.

FIG. 4 shows in detail that part of the syringe comprising the reservoir, with an injector which has protuberances.

In FIGS. 1 and 2, the syringe is shown vertically, with the injection system or injector 4 being directed downward: this defines the downstream direction of the syringe, the opposite direction being upstream.

The syringe 1 comprises a body 8 in which a cylindrical reservoir 2 containing the liquid active principle 6 is housed.

Mounted on the downstream end of the body 8 is an injector 4 which, in this example, comprises four injection ducts such as the duct 11. The downstream face of the injector is covered with an external protection to ensure that asepsis of the syringe is maintained; this protection comprises a membrane, made of elastomer, applied on the outer face of the injector by a fine metal protective cap crimped around the end of the syringe. This protection will be removed before injection. At its upstream end, the body 8 is fixed to a driving means 70 which, in this example, is of the pyrotechnic gas generator type, which will be described below.

The reservoir 2 in this example is a tube made of a material which is transparent and compatible with the liquid active principle, this material being, for example, glass of type I or II from the pharmacopeia, although it is possible to use any other transparent and compatible material.

The reservoir 2 is closed off at its upstream part by a displaceable closure element 3. This closure element 3 is of the plunger stopper type conventionally used in syringes: this is a component produced by molding a suitable elastomer to form a plunger and comprising several lateral lips or beads to ensure leaktightness (these elements are not detailed in the figures). The surface of this closure element can be treated in a known manner in order to facilitate its sliding in the reservoir. The materials conventionally used to produce the plunger stoppers are elastomers known from the pharmacopeia to be compatible with the active principle. These are, for example, chlorobutyls or bromobutyls whose Shore hardness is between about 45 and about 70.

The reservoir 2 is closed off at its downstream part by a traversable membrane 5. This traversable membrane 5 is pinched between the downstream edge of the reservoir 2 and the substantially plane upstream face of the injector 4 and thus renders the reservoir 2 leaktight. The traversable membrane 5 is produced using an elastomer or polymer compatible with the active principle chosen, for example, from the group already cited. The thickness of the membrane 5 is between about 0.2 mm and about 1.5 mm, said thickness preferably being between about 0.2 mm and about 0.4 mm.

The injector 4 in this example is screwed onto the body 8. The injector comprises four injection ducts, such as the duct 11, which are distributed on a cylinder whose axis coincides with that of the reservoir 2. In this example, the ducts are shown parallel to the axis of the reservoir and are of substantially constant cross section; without departing from the scope of the present invention, they can have more complex designs for reasons, and in embodiments, explained elsewhere. However, generally for these injection ducts, the ratio of the length to the diameter is greater than about ten, or even several tens. The ducts preferably comprise an inlet cavity 12 at the upstream end. Each duct can have a cavity, or one cavity can be common to several ducts or to all the ducts, in which latter case it will be a circular groove, taking into consideration what has been described concerning the arrangement of the ducts. As will be seen from the detail in FIG. 2, the role of this inlet cavity is to permit tearing or opening of the pre-pierced area of the membrane 5 opposite the duct 11 when the liquid is subjected to the injection pressure. It will be noted that a cell is created on the duct, favoring the control of the distance of cohesion of the jet, as we have explained elsewhere.

On the downstream face of the injector 4, that is to say the face which will bear on the skin of the subject who is to be treated, the ducts 11 open out through protuberances which, if appropriate, join together to form a circular flange. This arrangement favors a more uniform bearing on the skin and makes it possible to tolerate a small defect in the perpendicular attitude of the syringe with respect to the skin, without impairing the quality of the injection.

In this example, the driving means 70 acts on the closure element 3 by way of a plunger 10, shown in part in cross section. This plunger is made of metal or of hard plastic material, for example Teflon®, and it comprises sealing means, shown here simply by an O-ring seal. With its sealing means, this plunger ensures that the combustion gases from the pyrotechnic generator do not come into contact with the closure element 3. This plunger also serves as evidence of functioning when it appears in the window of the body 8. This role of visual evidence can also be assured by the displaceable closure element itself.

Finally, FIGS. 1 and 2 show a particular case of mounting the reservoir 2 in the body 8. The reservoir 2, centered in the injector 4 and placed in the body 8, is enveloped with an intermediate material 9 which, when the assembly is mounted on the body 71 of the driving means 70, will be compressed by the lip of the body 71: this compression of the intermediate material 9 at this instant ensures the fritting of the reservoir 2 and allows the latter to resist the high pressures of injection during functioning of the driving means.

We will now describe the main elements of the pyrotechnic generator. It comprises the body 71, and a pyrotechnic charge 72 whose combustion is initiated by a primer 73 impacted by a striker 74. The primer 73 is covered by a primer holder 80. In the initial position, the striker 74 is retained in the striker guide 75, screwed integrally with the body 71, by at least one ball, such as the ball 77, which is partially engaged in a groove of the striker. The percussion device comprises a push button 78 with a groove 79 and an inner spring 76. The push button 78 slides on the outside of the striker guide 75 and it is retained by studs which move in lateral grooves. This push button 78 is in this case the trigger member.

In order to initiate the combustion of the pyrotechnic charge 72, it is of course possible, without departing from the scope of the invention, to use initiating devices other than the striker device described here. Without going into details, and without wishing to imply any limitation, we will cite here, as examples, devices with initiation by electric battery or devices with piezoelectric initiation.

If appropriate, the pyrotechnic gas generator can be replaced by a gas generator consisting of a compressed gas reservoir which is closed by a fast-opening valve. The trigger member will open said valve, and the compressed gases in the reservoir will expand and act on the thrust means.

For use after having removed the aseptic stopper and placing the syringe on the skin of the subject who is to be treated, the operator presses with his thumb on the push button 78 which moves down and compresses the spring 76. The push button moves down until the groove 79 arrives at the level of the groove containing the balls, for example the ball 77, which balls disengage into the groove 79 and release the striker, which will violently impact the primer 73 whose initiation fires the pyrotechnic charge 72. The striker bearing on the primer holder 80 retains the latter in its seat and ensures leaktightness: the combustion gases do not rise back toward the push button.

FIG. 3 shows in detail the opening of a membrane in line with a pre-pierced area. Circular holes are pierced in the membrane, the diameter of these holes being between about 100 μm and about 300 μm. On account of the elasticity of the elastomer of the membrane, the pre-pierced areas remain closed and relatively leaktight. At the head of the duct 11, opposite a pre-pierced area of the membrane, there is an inlet cavity 12 of substantially conical shape whose height is equal to about twice the diameter of the base. Under the effect of the pressure transmitted to the liquid when the driving means is put into operation, the edge of the pre-pierced area of the membrane deforms and comes to bear on the wall of the conical cavity at the head of the duct. At the inlet to the duct there thus forms a cell which produces perturbations and turbulence in the flow; these phenomena contribute to controlling the distance of cohesion of the jet.

FIG. 4 shows a view of a detail of another embodiment of the invention. In this example, the injector of the syringe comprises protuberances 46 at the upstream end of each injection duct 41; in this example the protuberance has a very simple shape, namely that of a truncated cone. The traversable membrane 45, which comprises pre-pierced zones opposite the injection ducts, bears on these protuberances. The outer perimeter of the membrane 45 is pinched between the tube of the reservoir and a peripheral shoulder of the injector. The membrane is wedged angularly in relation to the injection by a system of studs or pins (not shown in this diagram) in such a way that the pre-pierced areas of the membrane lie opposite the injection ducts. Under the effect of the pressurization of the liquid by the driving means, the membrane will be crushed on the injector, and the pre-pierced zones are opened by the conical protuberances; the edges of the pre-pierced zones spread apart to allow the liquid to pass through.

What is claimed is:

1. A needleless syringe for injection of a liquid active principle contained in a cylindrical reservoir closed at its upstream part by a closure element which can be displaced by a driving means, and closed at its downstream part by a transversable membrane compatible with the active principle and covering an injector which comprises at least one injection duct, and this reservoir being made integral with the body of the syringe, said syringe being characterized in that the reservoir is tubular, the membrane is pinched between the downstream edge of the reservoir and a substantially plane upstream face of the injector, the membrane comprises pre-pierced areas opposite each at least one injection duct, and each pre-pierced area remains closed and leaktight until the liquid is pressurized.

2. The needleless syringe as claimed in claim 1, characterized in that the membrane covers at least two injection ducts the upstream ends of which are situated on the same circle centered on the axis of the cylindrical reservoir.

3. The needleless syringe as claimed in claim 1, characterized in that the membrane comprises a circular slit centered on the axis of the reservoir, this slit being opposite the upstream ends of the injection ducts and remaining closed and leaktight until the liquid is pressurized.

4. The needleless syringe as claimed in claim 1, characterized in that an inlet cavity is delimited by a surface of revolution whose height and diameter at the level of the upstream face are greater than the thickness of the membrane and less than three times this thickness.

5. The needleless syringe as claimed in claim 4, characterized in that the inlet cavities join and form a circular groove on the upstream face of the injector.

6. The needleless syringe as claimed in claim 5, characterized in that the circular groove has a height and a width which are greater than the thickness of the membrane and less than two times the thickness of the membrane.

7. The needleless syringe as claimed in claim 1, characterized in that the driving means acts directly on the upstream closure element.

8. The needleless syringe as claimed in claim 1, characterized in that the driving means acts on the upstream closure element by way of a plunger.

9. The needleless syringe as claimed in claim 1, characterized in that the driving means is a pyrotechnic gas generator.

10. The needleless syringe as claimed in claim 1, characterized in that the reservoir and the body form a single unit.

11. The needleless syringe as claimed in claim 1, characterized in that the reservoir is fitted in the body via an intermediate material when mounted on the driving means.

12. The needleless syringe as claimed in claim 1, characterized in that the body is transparent.

13. The needleless syringe as claimed in claim 1, characterized in that body comprises at least one window for viewing the contents of the reservoir.

* * * * *